(12) United States Patent
Hou et al.

(10) Patent No.: US 8,221,374 B2
(45) Date of Patent: Jul. 17, 2012

(54) URINARY INCONTINENCE DEVICE APPLICATOR

(75) Inventors: Mari Hou, Hoboken, NJ (US); Raymond J. Hull, Jr., Hampton, NJ (US); Paul B. Swick, Lebanon, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 13 days.

(21) Appl. No.: 12/059,724

(22) Filed: Mar. 31, 2008

(65) Prior Publication Data

US 2009/0247929 A1   Oct. 1, 2009

(51) Int. Cl.
*A61F 13/15*   (2006.01)
*A61F 13/20*   (2006.01)

(52) U.S. Cl. .................. 604/385.17; 604/904

(58) Field of Classification Search ............... 604/13–18, 604/385.17–385.18, 904
See application file for complete search history.

(56) References Cited

U.S. PATENT DOCUMENTS

| | | | |
|---|---|---|---|
| 3,643,661 A | 2/1972 | Crockford | |
| 3,706,311 A | 12/1972 | Kokx et al. | |
| 4,048,998 A * | 9/1977 | Nigro | 604/14 |
| 4,143,656 A | 3/1979 | Holmes | |
| 4,198,978 A | 4/1980 | Nigro | |
| 4,398,532 A | 8/1983 | Sweeney, III | |
| 4,447,222 A | 5/1984 | Sartinoranont | |
| 5,041,080 A * | 8/1991 | Shimatani et al. | 604/13 |
| D349,339 S * | 8/1994 | Youtsler et al. | D24/133 |
| 5,483,976 A | 1/1996 | McLaughlin et al. | |
| 5,618,256 A | 4/1997 | Reimer | |
| 5,659,934 A | 8/1997 | Jessup et al. | |
| 5,785,640 A | 7/1998 | Kresch et al. | |
| 5,807,372 A | 9/1998 | Balzar | |
| 5,873,971 A | 2/1999 | Balzar | |
| 6,645,136 B1 | 11/2003 | Zunker et al. | |
| 6,648,846 B2 * | 11/2003 | Binner et al. | 604/15 |
| 6,695,763 B2 | 2/2004 | Zunker et al. | |
| 6,739,340 B1 | 5/2004 | Jensen et al. | |
| 6,969,380 B1 | 11/2005 | Zunker | |
| 2004/0077924 A1 | 4/2004 | Zunker et al. | |
| 2004/0078013 A1 | 4/2004 | Zunker et al. | |
| 2004/0122745 A1 | 6/2004 | Hantke et al. | |
| 2005/0096721 A1 | 5/2005 | Mangin et al. | |
| 2006/0004320 A1 | 1/2006 | Berg et al. | |
| 2007/0128254 A1 | 6/2007 | Heuer et al. | |
| 2007/0203429 A1 | 8/2007 | Ziv | |
| 2008/0009662 A1 | 1/2008 | Bartning et al. | |
| 2008/0009663 A1 | 1/2008 | Bartning et al. | |
| 2008/0009664 A1 | 1/2008 | Bartning et al. | |
| 2008/0009666 A1 | 1/2008 | Bartning et al. | |

(Continued)

FOREIGN PATENT DOCUMENTS

EP   0 104 039 A   3/1984

(Continued)

OTHER PUBLICATIONS

European Search report dated Jun. 16, 2011, for corresponding EP application 09250952.0.

(Continued)

*Primary Examiner* — Michele M Kidwell

(57) ABSTRACT

A urinary incontinence device applicator has an insertion barrel; a plunger slidable within the insertion barrel; means to indicate appropriate insertion depth of the insertion barrel associated therewith into a user's vagina; and means to indicate appropriate orientation of the insertion barrel associated therewith.

13 Claims, 7 Drawing Sheets

U.S. PATENT DOCUMENTS

| | | | |
|---|---|---|---|
| 2008/0009814 A1 | 1/2008 | Bartning et al. | |
| 2008/0009931 A1 | 1/2008 | Bartning et al. | |
| 2008/0033230 A1 | 2/2008 | Bartning et al. | |
| 2008/0033231 A1 | 2/2008 | Bartning et al. | |
| 2008/0033337 A1* | 2/2008 | Dougherty et al. | 604/15 |
| 2008/0281149 A1 | 11/2008 | Sinai et al. | |
| 2009/0247815 A1 | 10/2009 | Hou et al. | |
| 2009/0247928 A1 | 10/2009 | Bartning et al. | |

FOREIGN PATENT DOCUMENTS

| | | |
|---|---|---|
| EP | 1 688 112 A | 8/2006 |
| GB | 557035 A | 11/1943 |
| WO | WO 1995/05790 A | 3/1995 |
| WO | WO 2000/67662 A | 11/2000 |
| WO | WO 2002/26160 A | 4/2002 |
| WO | WO 2004/103213 A | 12/2004 |
| WO | WO 2005/087153 A | 9/2005 |
| WO | WO 2005/087154 A | 9/2005 |
| WO | WO 2006/005009 A | 1/2006 |
| WO | WO 2006/097935 A | 9/2006 |
| WO | WO 2007/146270 A | 12/2007 |
| WO | WO 2009/044394 A | 4/2009 |

OTHER PUBLICATIONS

In the USPTO U.S. Appl. No. 12/059,774, filed on Mar. 31, 2008 the restriction requirement dated Jun. 5, 2009.

In the USPTO U.S. Appl. No. 12/059,774, filed on Mar. 31, 2008 the non-final office action dated Mar. 27, 2012.

In the USPTO U.S. Appl. No. 12/757,308, filed on Apr. 9, 2010 the final office action dated Mar. 27, 2012.

In re the USPTO U.S. Appl. No. 12/059,607 (US 7935098) the non-final rejection dated Sep. 29, 2009.

In re the USPTO U.S. Appl. No. 12/059,607 (US 7935098) the final rejection dated Mar. 19, 2010.

In re the USPTO U.S. Appl. No. 12/059,607 (US 7935098) the non-final rejection dated Aug. 20, 2010.

In re the USPTO U.S. Appl. No. 12/059,607 (US 7935098) the final rejection dated Jan. 31, 2011.

In re the USPTO U.S. Appl. No. 12/059,607 (US 7935098) the Notice of Allowance dated Feb. 18, 2011.

In re the USPTO U.S. Appl. No. 12/059,607 (US 7935098) the Notice of Allowance dated Mar. 22, 2011.

In re the USPTO U.S. Appl. No. 12/059,774 (US 2009/0247815A1) the non-final rejection dated Jul. 17, 2009.

In re the USPTO U.S. Appl. No. 12/059,774 (US 2009/0247815A1) the final rejection dated Jan. 11, 2010.

In re the USPTO U.S. Appl. No. 12/757,308 (US 2010/0197997A1) the non-final rejection dated Dec. 12, 2011.

* cited by examiner

URINARY INCONTINENCE DEVICE APPLICATOR

BACKGROUND OF THE INVENTION

The present invention relates to an applicator for urinary incontinence devices. The applicator is useful for placing the device in the vagina in the correct position to enable the device to function.

Tampons are absorbent articles that are inserted into a woman's vagina to absorb blood while she is menstruating. Urinary incontinence devices are inserted into a woman's vagina to reduce or inhibit urinary incontinence. Applicators may be used to ease the insertion of urinary incontinence devices and tampons. Applicators typically include a generally cylindrical barrel for holding the tampon or device and placing in the vagina, and a plunger for expelling the device or tampon into the vagina. Cardboard and plastic applicators are known in the art.

The placement and orientation of a urinary incontinence device is important in enabling the device to function properly. For some devices, it is important that the device is deployed in a position where pressure is applied to the urethra at the neck of the bladder. As some urinary incontinence devices expand to generate force, it is important that the device is oriented so that the force is directed toward the urethra. Therefore, the urinary incontinence device needs to be deployed in the right location and in the correct orientation.

Tampon applicators are known to contain finger grip portions. World Patent Application number WO2006/005009A1 discloses an applicator with indicia for low placement in the vagina on the barrel. There is a continuing need for a urinary incontinence applicator that deploys the device in the right location and in the correct orientation.

SUMMARY OF THE INVENTION

The present invention provides a urinary incontinence device applicator. The applicator has an insertion barrel; a plunger slidable within the insertion barrel; means to indicate appropriate insertion depth of the insertion barrel associated therewith into a user's vagina; and means to indicate appropriate orientation of the insertion barrel associated therewith.

In another embodiment, the invention provides a system to provide a urinary incontinence device. The system includes an applicator and an intravaginal urinary incontinence device substantially contained within the applicator. The applicator includes a substantially tubular insertion barrel having an insertion end, an opposite gripper end, and a longitudinal axis; a plunger extending from the gripper end of and slidable within the insertion barrel; an insertion depth indicator arranged and configured to bear against a user's labia majora extending from the insertion barrel proximate the gripper end; and means to indicate appropriate orientation of the insertion barrel associated with the applicator. The means to indicate appropriate orientation of the insertion barrel is arranged and configured to deliver the intravaginal urinary incontinence device in an appropriate orientation into the user's vagina.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF PREFERRED EMBODIMENTS

Figure 1:
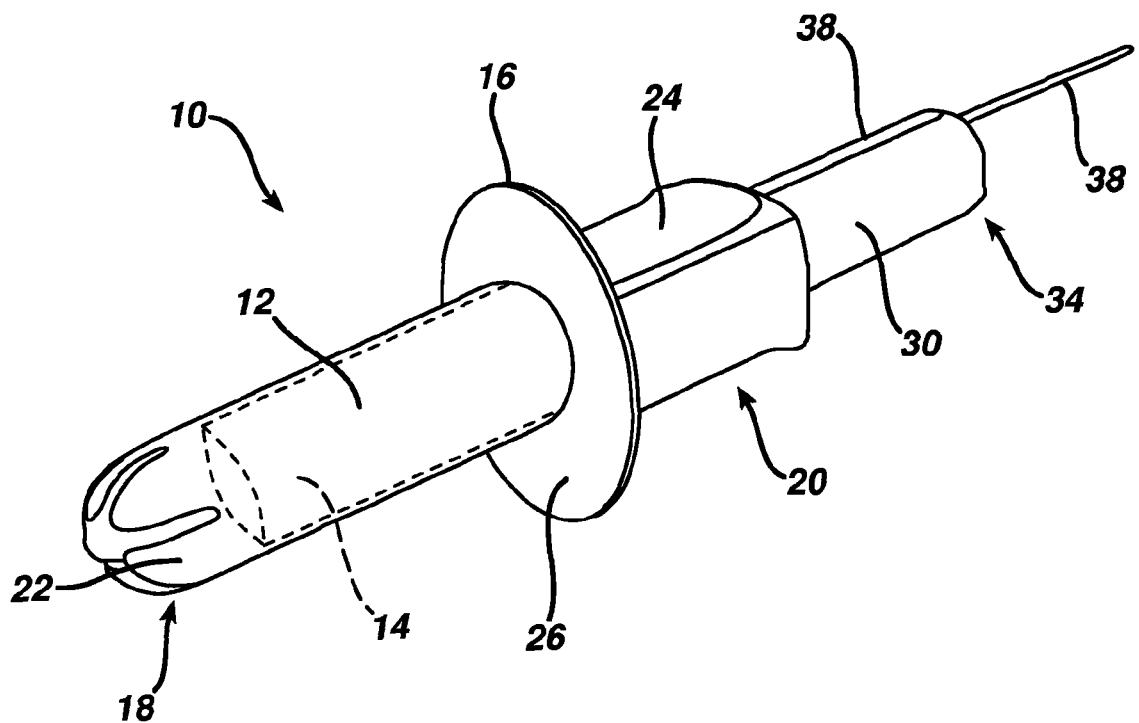
FIG. 1 is a perspective view of an applicator of the present invention.
Figure 2:
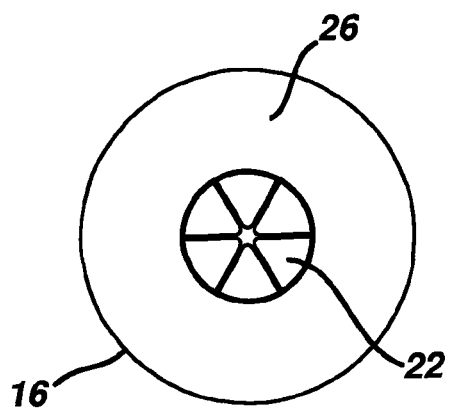
FIG. 2 is a front view of the applicator of FIG. 1.

With reference to FIGS. 1-2, applicators 10 according to the present invention include an insertion barrel 12. The insertion barrel is sized and shaped to contain the urinary incontinence device 14 within it, and it has an external insertion depth indicator 16. The length of the barrel (to the base of petals, if present, at the insertion end) may range from about 20 mm to about 100 mm, preferably about 40 mm to about 60 mm, most preferably about 50 mm. The diameter or the barrel may range from about 5 mm to about 20 mm, preferably about 18 mm to about 20 mm. The thickness of the barrel is sufficient to withstand the pressure exerted by the device, and may range, for example, from about 1 mm to about 3 mm. The barrel has an insertion end 18 to east the insertion of the applicator into the vagina, and an opposite, gripper end 20 into which the urinary incontinence device can be loaded. The insertion end 18 may be open, or as is known in the tampon art, may have petals 22 (not required) for easing insertion of the applicator and for retaining the device until deployment.

The insertion barrel may be made from any suitable material, such as polyethylene, polypropylene, acetal resins, styrene copolymers (including rubber-modified glassy plastics such as ABS [a two-phase system of styrene-acrylonitrile copolymer and styrene-budatidene copolymer]). The insertion depth indicator may be molded into the barrel or may be formed separately and attached to the applicator through conventional methods, such as adhesives, friction fits and the like.

The insertion depth indicator 16 is a raised element on the insertion barrel surface, oriented generally perpendicular to the longitudinal axis of the insertion barrel (and thus, the direction of insertion). This provides a tactile feedback when the insertion is completed, e.g., bearing against the user's labia majora 17. While a small height of discontinuity is sufficient to give a tactile feedback, the height of the discontinuity also defines a bearing surface that can be held against the body to maintain the correct insertion depth during deployment of the device. The height of the discontinuity may range from 2 mm to 20 mm.

Figure 3:
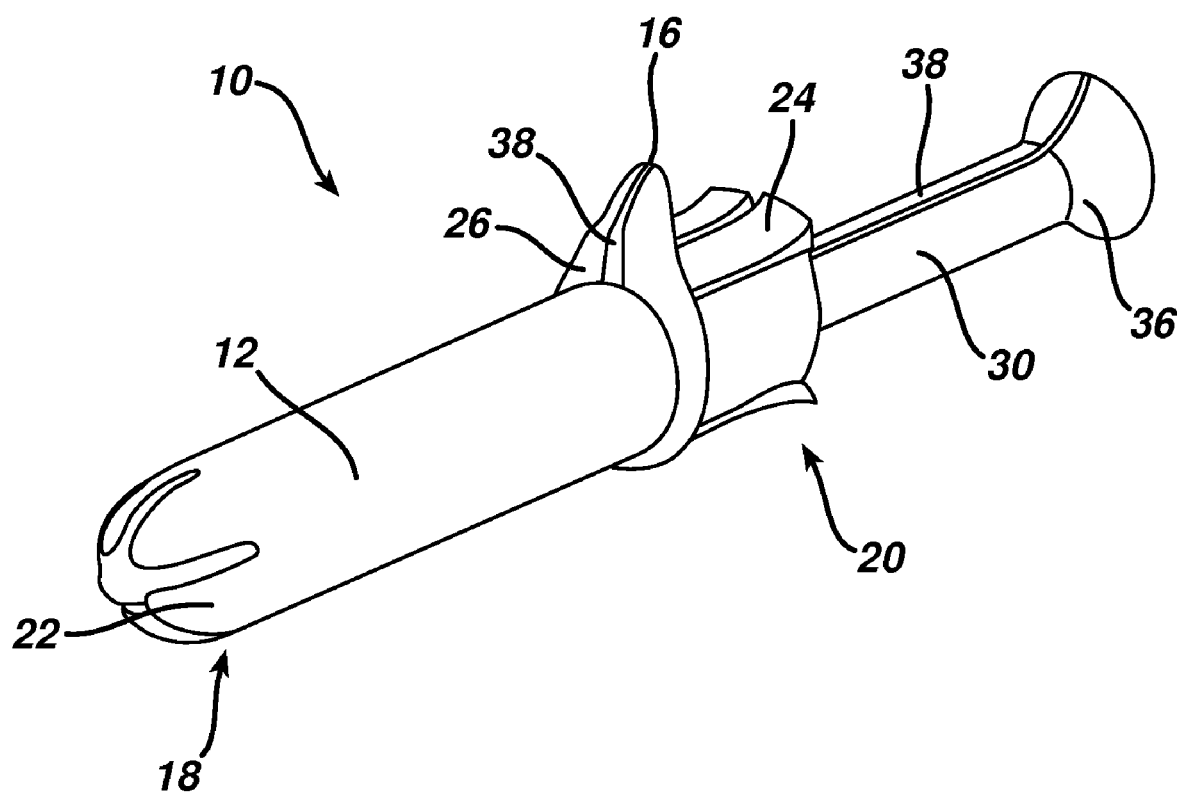
FIG. 3 is a perspective view of a second applicator of the present invention.
Figure 4:
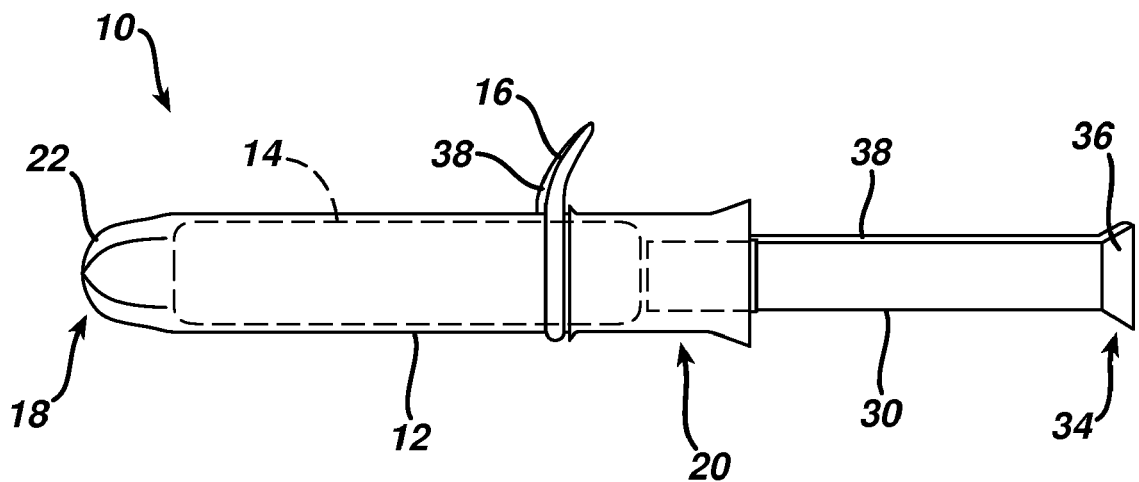
FIG. 4 is a side elevation of the applicator of FIG. 3.
Figure 5:
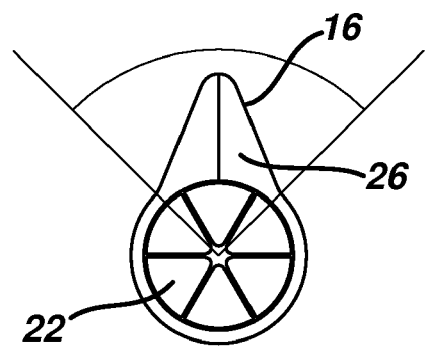
FIG. 5 is a front view of the applicator of FIG. 3.

The insertion depth indicator may be made from any suitable material, such as polyethylene, polypropylene, a variety of copolymers, silicone, and elastomeric materials, such as ethylene propylene diene monomer and the like. The insertion depth indicator may be molded into the barrel or may be formed separately and attached to the applicator through conventional methods, such as adhesive, friction fit, and the like. The insertion depth indicator may also function as and/or incorporate a finger grip 24. The insertion depth indicator is positioned such that the device is deployed in the proper position within the vagina. The distance between the insertion end of the barrel 12 and the insertion depth indicator 16 may range from about 40 mm to about 80 mm, for example about 60 mm. The amount that the insertion depth indicator extends about the circumference of the insertion barrel, the "angle of wrap," α, may vary. An angle of wrap, α, of 360° shown in FIGS. 1-2, provides the largest and most stable bearing surface 26; however, smaller angles, e.g., about 90° as shown in FIGS. 3-5, require less material and are more convenient to stack and store. The bearing surface 26 can also consist of multiple segments spaced around the circumference of the insertion barrel. These multiple segments can also have different heights of the indicator.

Figure 6A:
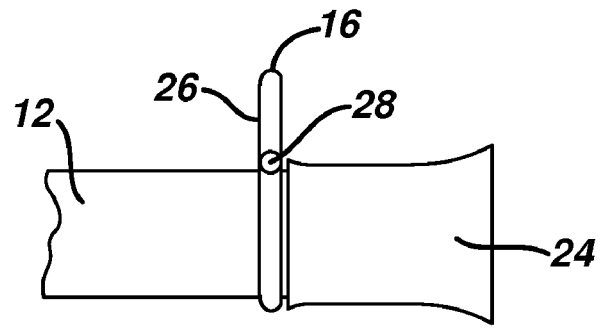
FIGS. 6A-C is a series of partial side elevations of an alternative embodiment of the applicator of the present invention illustrating different angular positions of the insertion depth indicator.
Figure 6B:
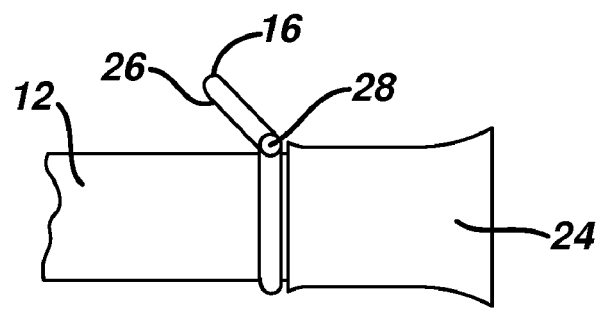
Figure 6C:
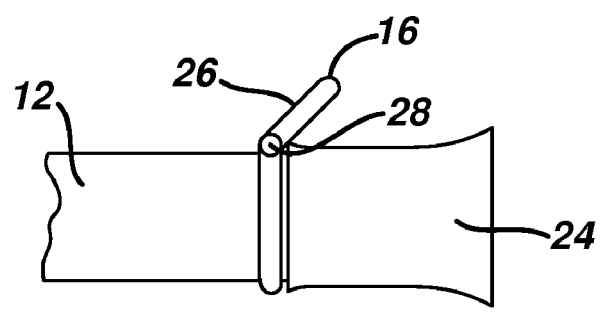
Figure 7A:
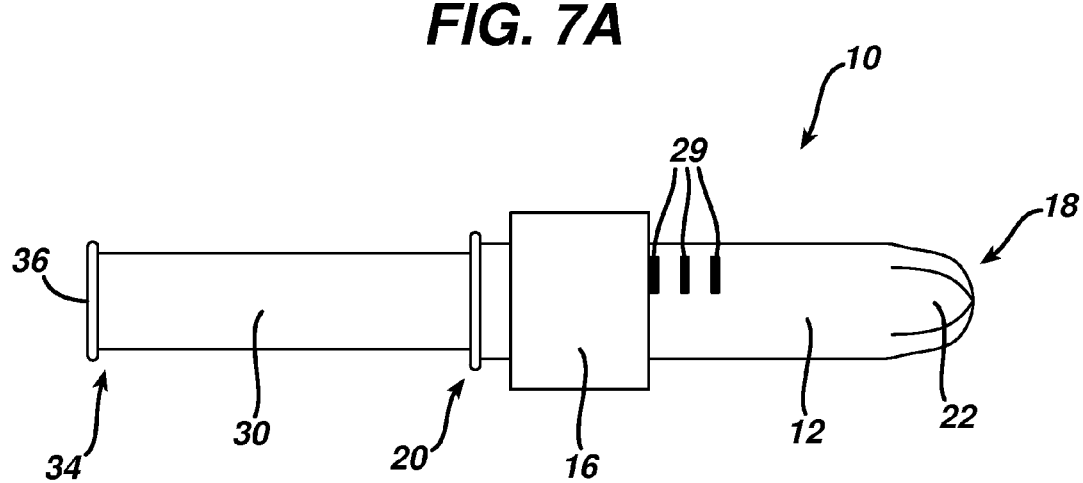
FIGS. 7A-B are side elevations of another alternative embodiment of the applicator of the present invention illustrating different longitudinal positions of the insertion depth indicator.
Figure 7B:
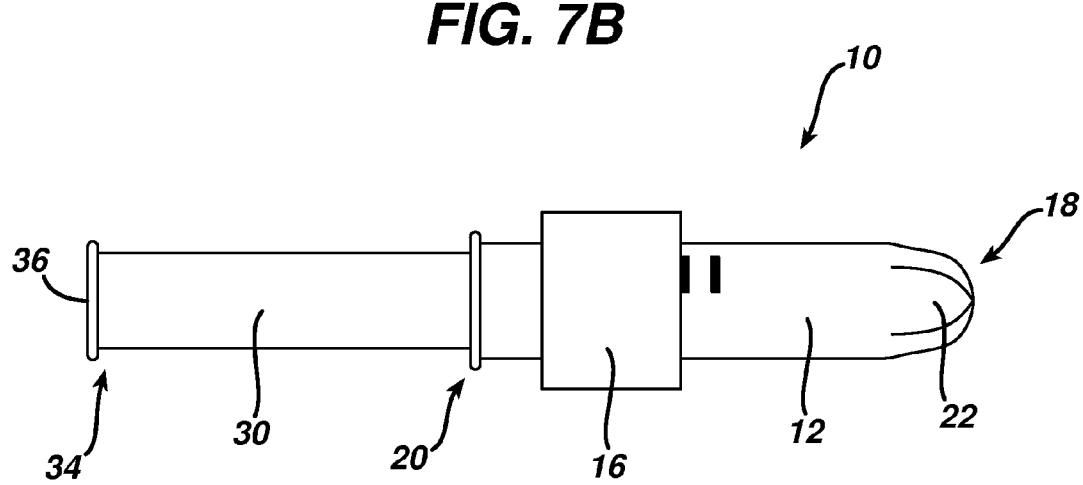

The external depth indicator may be integral with the barrel (including permanently and immovably attached), or it may be adjustable, if desired. This may be helpful to improve comfort for the user. As exemplified in FIGS. 6A-C, it may be desirable to permit the indicator 16 to pivot about a hinge 28. FIG. 6B shows the indicator 16 pivoted into a forward position, and FIG. 6C shows it pivoted back toward the gripper end 20. The choice may depend upon the position of the woman during insertion of the device. The angle may depend on the woman's particular anatomy—the curves of her labia. In addition, the woman may desire to rotate the indicator 16 around the barrel 12 to bear differently on her body. Finally as shown in FIGS. 7A-B, the woman may desire to change the location of the indicator 16 along the length of the barrel 12 if she desires to fine-tune the insertion depth based upon her knowledge of her own anatomy. To aid in this adjustment, indicia 29 may be provided on the insertion barrel 12.

Applicators according to the present invention also include a deployment plunger 30, an elongate device, designed to slidingly fit within the barrel 12. The plunger 30 has a leading end 32 to bear against and to deploy the incontinence device and an opposite end 34 having a stop 36 to prevent the plunger from being pushed too far and to ensure proper placement of the device in the vagina. The plunger 30 is moved axially into the insertion barrel 12 to deploy the device from the insertion end 18 into the vagina. The barrel 12 and plunger 30 may be made from any suitable material. For example, the barrel and plunger may be molded from conventional thermoplastic materials such as, but not limited to, polyethylene, polypropylene and a variety of copolymers.

Figure 8:
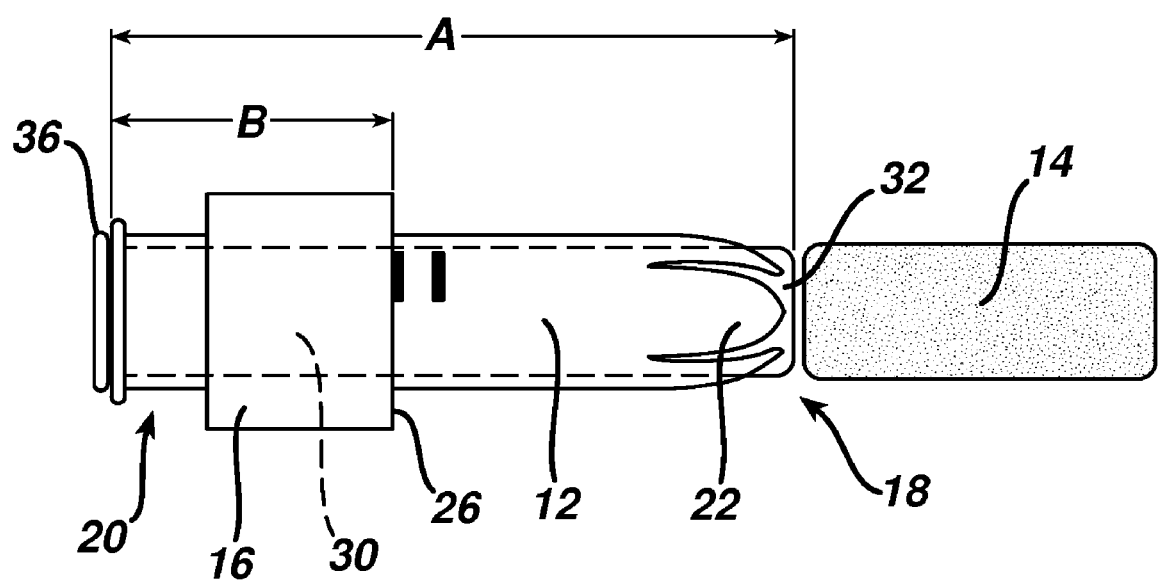
FIG. 8 is a side elevation of the applicator of FIG. 7B as the urinary incontinence device is deployed.
Figure 9:
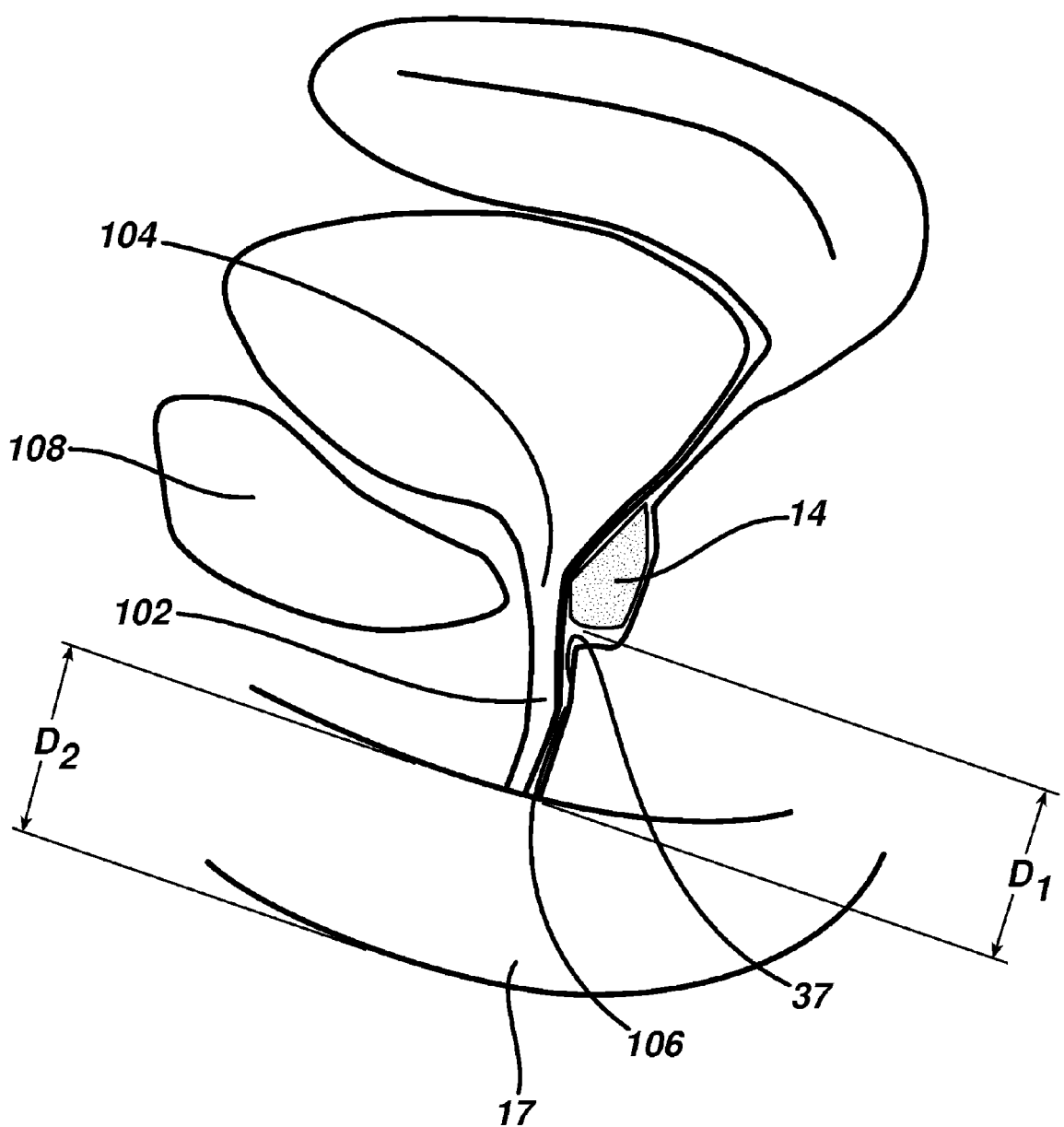
FIG. 9 is a sagittal cross-section of the female pelvis illustrating relationship between the vagina, bladder, urethra, pubic bone, urethro-vesical junction, and labia.

Referring to FIG. 8, the insertion depth of the base 37 of the incontinence device will be determined by two dimensions when the applicator is fully inserted and deployed. Dimension "A" is the axial length of the plunger from the plunger stop 36 to the leading end 32 of the plunger 30 where it contacts the device 14. Dimension "B" is the axial length from the plunger stop 36 to the bearing surface 26 of the insertion depth indicator 16. The insertion depth of the base 37 of the device from the body exterior is A-B. The applicator is designed so that the portion of the device 14 in the vagina 100 that applies pressure to the urethra 102 is placed at the urethro-vesical junction 104, and/or the base 37 of the device 14 is at least 10 mm to 20 mm, for example 15 mm above the hymenal opening 106, as shown in FIG. 9 (dimension $D_1$). To this dimension is added the distance $D_2$ between the outer surface of the labia majora 17 and the hymenal opening.

Applicators according to the present invention may also include an orientation indicator 38. The orientation indicator 38 is utilized to place the incontinence device in the vagina such that when it is deployed, the portion of the device that applies pressure exerts pressure on the urethra-vesical junction, and any anchoring members lie on the lateral sides of the vagina. The orientation indicator 38 clearly marks the orientation of the device within the applicator. The indicator may be a raised line, a colored line, dots, embossments, or any suitable mark or shape that indicates orientation. The orientation indicator may be on any or all of a conventional finger grip, the insertion depth indicator, and the barrel itself. If the device is aligned with the orientation indicator when it is within the applicator, then it will be aligned to the body after insertion. When the orientation indicator 38 is part of the insertion depth indicator 16, the orientation indicator 38 may be part of the shape of the insertion depth indicator 16. For example, the insertion depth indicator 16 may have an apex, which is the indicator.

Suitable urinary incontinence devices for use with the applicators of the present invention include, but are not limited to, devices taught in co-pending US Patent Applications Attorney Docket, PPC5238, U.S. application Ser. No. 11/456, 376, filed, Jul. 10, 2006; U.S. application Ser. No. 11/776, 178, filed, Jul. 11, 2007; U.S. application Ser. No. 11/456, 390, filed, Jul. 10, 2006; U.S. application Ser. No. 11/456, 402, filed, Jul. 10, 2006; U.S. application Ser. No. 11/456, 424, filed, Jul. 10, 2006; U.S. application Ser. No. 11/776, 185, filed, Jul. 11, 2007; U.S. application Ser. No. 11/456, 433, filed, Jul. 10, 2006; and U.S. application Ser. No. 11/456, 442, filed, Jul. 10, 2006.

Examples are set forth below to further illustrate the nature of the invention and the manner of carrying it out. However, the invention should not be considered as being limited to the details thereof.

EXAMPLE 1

Barrel and plunger components according to FIGS. 7A-B were molded out of linear low-density polyethylene (LLDPE) with a 1% modified polyethylene slip additive. Samples of these components were also molded out of high-density polyethylene (HDPE) and low-density polyethylene (LDPE). The LLDPE however was the material of choice for actual use testing. The collar and finger grip components also utilized single cavity injection molds. A finger-grip sleeve and the insertion depth indicator collar were both designed to be friction fit attached to the applicator, and the distance from the collar to the base of the petals was about 50 mm. The material utilized was a 65-durometer thermoplastic elastomer under the trade name of C-flex.

EXAMPLE 2

A use test was performed with 20 women to mainly determine the ability of the applicators of the present invention to correctly place the device in the body. An intra-vaginal incontinence device prototype was inserted into the vagina utilizing the applicator of Example 1. The first test was for the subject to insert the device via the provided applicator and instructions. For this test, a physician checked the placement of the device post insertion and assessed whether the device was too high, at the correct location, or too low.

Referring again to FIG. 9, the device 14 was considered to be too high if the base 37 of the device 14 in the vagina 100 was located above the urethro-vesical junction 104. This was assessed by palpation and/or visualization. If the doctor could feel the pubic bone 108 before the base 37 of the device 14, the device was considered to be too high. The device 14 was considered to be at the correct location if a working portion of the device 14 was at the urethro-vesical junction 104. If the doctor could see that the device 14 was at least 10 mm ($D_1$) into the vagina 100 past the hymenal ring 106, or if the doctor could feel the base 37 of the device before feeling the pubic bone 108, the device 14 was considered to be at the correct location. The device was considered to be too low if it was placed outside the hymenal ring 106 or less than 10 mm into the vagina 100 past the hymenal ring 106.

If the device was placed incorrectly (too high or too low), the subject was asked to re-insert the device with feedback on the initial placement. The results of this study of placement via applicator are shown in Table 1 below.

TABLE 1

| Insertion | % With Correct Placement |
|---|---|
| Initial | 75 (15/20) |
| Second | 40 (2/5) |
| Total | 85 (17/20) |

Based on the data above, it was determined that the devices of the present invention are effective at placing urinary incontinence devices in the proper position within the vagina, either initially or with guidance and practice.

We claim:

1. A system to provide a urinary incontinence device comprising:
   a) an applicator comprising:
      i) a substantially tubular insertion barrel having an insertion end, an opposite gripper end, and a longitudinal axis;
      ii) a plunger extending from the gripper end of and slidable within the insertion barrel and having a leading end to bear against and to deploy the incontinence device; and
      iii) an insertion depth indicator arranged and configured to bear against a user's body extending from the insertion barrel proximate the gripper end and incorporating an orientation indicator;
   b) an intravaginal urinary incontinence device substantially contained within the insertion barrel, wherein the orientation indicator of the insertion barrel marks the orientation of the urinary incontinence device and is arranged and configured to deliver the intravaginal urinary incontinence device in an appropriate orientation into the user's vagina such that a portion of the intravaginal urinary device applies pressure on the urethra-vesical junction and anchoring members of the device are laterally disposed in the vagina.

2. The applicator according to claim 1 wherein the insertion depth indicator is selected from the group consisting of a raised discontinuity, a finger grip and a collar.

3. The system according to claim 1 wherein the insertion depth indicator is integral with the insertion barrel.

4. The system according to claim 1 wherein the insertion depth indicator comprises a structure attached to the insertion barrel.

5. The system according to claim 4 wherein the insertion depth indicator is adjustable.

6. The system according to claim 5 wherein the insertion depth indicator has a distal end that is capable of pivoting in a plane containing the longitudinal axis of the insertion barrel.

7. The system according to claim 5 wherein the insertion depth indicator is capable of rotating in a plane perpendicular to the longitudinal axis of the insertion barrel.

8. The system according to claim 5 wherein the insertion depth indicator is capable of sliding along the insertion barrel.

9. The system according to claim 1 wherein the orientation indicator further includes a raised line, a colored line, dots, or embossments.

10. The system according to claim 1 wherein the orientation indicator is part of the shape of the insertion depth indicator.

11. A system to provide a urinary incontinence device comprising:
    a) an applicator comprising:
       i) a substantially tubular insertion barrel having an insertion end, an opposite gripper end, and a longitudinal axis;
       ii) a plunger extending from the gripper end of and slidable within the insertion barrel and having a leading end to bear against and to deploy the incontinence device; and
       iii) an insertion depth indicator arranged and configured to bear against a user's body extending from the insertion barrel proximate the gripper end and incorporating an orientation indicator;
    b) an intravaginal urinary incontinence device substantially contained within the insertion barrel, wherein the orientation indicator of the insertion barrel marks the orientation of the urinary incontinence device and is arranged and configured to deliver the intravaginal urinary incontinence device in an appropriate orientation into the user's vagina such that a portion of the intravaginal urinary device applies pressure on the urethra-vesical junction and anchoring members of the device are laterally disposed in the vagina,
wherein the insertion depth indicator has an apex which forms the orientation indicator.

12. The system according to claim 11 wherein the insertion depth indicator is integral with the insertion barrel.

13. The system according to claim 11 wherein the orientation indicator further includes a raised line, a colored line, dots, or embossments.

* * * * *